(12) United States Patent
Brasch et al.

(10) Patent No.: US 11,513,020 B1
(45) Date of Patent: Nov. 29, 2022

(54) PRESSURE-SENSITIVE PAD WITH CALIBRATION UNIT

(71) Applicant: J. Brasch Co., LLC, Lincoln, NE (US)

(72) Inventors: John Joseph Brasch, Lincoln, NE (US); Gordon Smith, Jr., Lincoln, NE (US); Harold Todd Tyler, Lincoln, NE (US)

(73) Assignee: J. Brasch Co., LLC, Lincoln, NE (US)

( * ) Notice: Subject to any disclaimer, the term of this patent is extended or adjusted under 35 U.S.C. 154(b) by 0 days.

(21) Appl. No.: 17/854,732

(22) Filed: Jun. 30, 2022

Related U.S. Application Data

(60) Provisional application No. 63/216,600, filed on Jun. 30, 2021.

(51) Int. Cl.
*G01L 1/22* (2006.01)
*G01L 25/00* (2006.01)

(52) U.S. Cl.
CPC ............... *G01L 25/00* (2013.01); *G01L 1/22* (2013.01)

(58) Field of Classification Search
CPC .................................. G01L 25/00; G01L 1/22
See application file for complete search history.

(56) References Cited

U.S. PATENT DOCUMENTS

| | | | | |
|---|---|---|---|---|
| 8,419,660 B1* | 4/2013 | Shaw | ...................... | A61B 5/1115 600/595 |
| 8,919,211 B1* | 12/2014 | Hanson | ..................... | G01L 25/00 73/862.626 |
| 11,076,764 B1* | 8/2021 | Goubran | ............... | A61B 5/1102 |
| 2014/0090489 A1* | 4/2014 | Taylor | ..................... | G01L 1/142 73/862.626 |
| 2015/0000044 A1* | 1/2015 | Morimura | ............. | G01L 27/005 5/710 |
| 2015/0250327 A1* | 9/2015 | Boyd | ................... | A47C 27/088 705/26.7 |
| 2017/0098048 A1* | 4/2017 | Brosnan | ................. | G16H 40/63 |
| 2018/0125413 A1* | 5/2018 | Smith, Jr. | ............ | A61B 5/7282 |
| 2018/0263378 A1* | 9/2018 | Anastasov | ......... | G08B 21/0461 |
| 2019/0269570 A1* | 9/2019 | Niederkofler | ....... | A61H 23/0263 |
| 2019/0331538 A1* | 10/2019 | Neel | .................... | H03K 17/962 |
| 2019/0365573 A1* | 12/2019 | Severns | ............. | G06K 7/10366 |
| 2020/0390403 A1* | 12/2020 | Halperin | ........... | G08B 21/0461 |
| 2022/0167875 A1* | 6/2022 | Cathelain | ........... | A61B 5/02405 |
| 2022/0260434 A1* | 8/2022 | Turunen | ................. | H05K 1/189 |

* cited by examiner

*Primary Examiner* — Max H Noori
*Assistant Examiner* — Masoud H Noori
(74) *Attorney, Agent, or Firm* — Michael D. Eisenberg

(57) ABSTRACT

A pressure sensitive pad configured to be placed under a mattress and configured to identify presence and absence of a threshold weight on the mattress. The pressure sensitive pad comprises a signal generator, a sensing zone, at least one variable matching resistor, a microcontroller unit (MCU). The signal generator configured to generate an electrical signal. The sensing zone has a sensing resistor with a first resistance which varies depending on a pressure applied on sensing zone. The variable matching resistor is in series with the sensing resistor and the signal generator, the variable matching resistor having a second resistance. The MCU has an analog-to-digital converter (ADC) configured for receiving and measuring a portion of the signal at an electrical junction between the sensing resistor an the at least one variable matching resistor, the MCU being configured to control the second resistance of the at least one variable matching resistor.

11 Claims, 6 Drawing Sheets

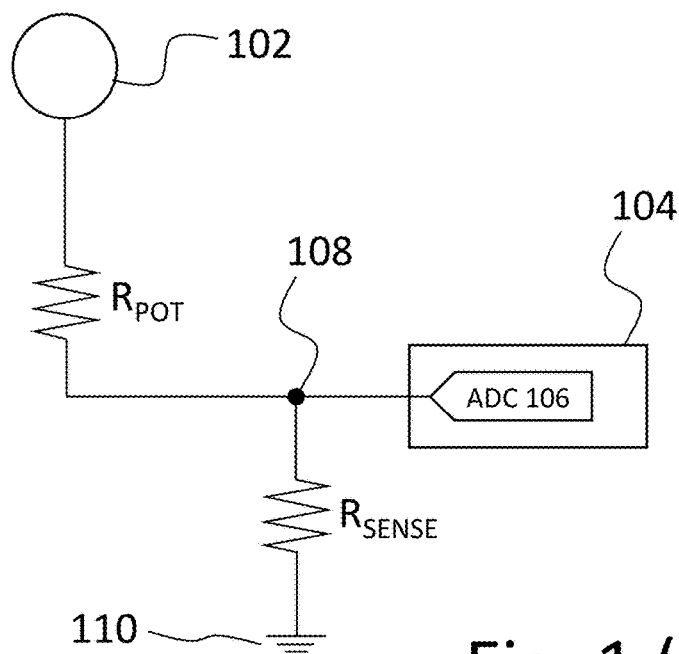
Fig. 1 (General art)
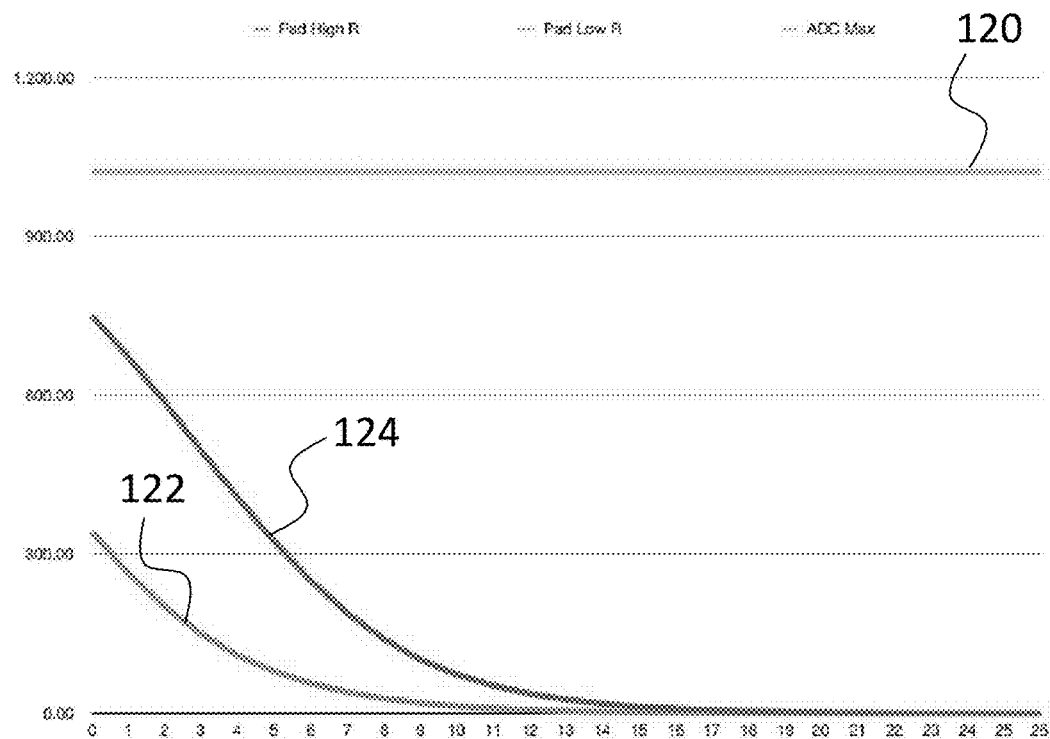
Fig. 2

PRESSURE-SENSITIVE PAD WITH CALIBRATION UNIT

CROSS-REFERENCES TO RELATED APPLICATIONS

The present application claims priority to U.S. Provisional Application Ser. No. 63/216,600 filed on Jun. 30, 2021, which is hereby incorporated in its entirety.

FIELD OF THE INVENTION

The present invention, in some embodiments thereof, relates to under-mattress pressure-sensitive pads, and in particular (but not limited to) to the calibration of under-mattress pressure-sensitive pad for use with a variety of mattresses.

BACKGROUND OF THE INVENTION

An under-mattress pressure-sensitive pad is a pad that is placed under a mattress to detect the presence of an object (such as person) on the mattress. The pad is configured to be used with a variety of mattresses having different shapes and weights, and still detect the presence of an object having a certain weight on the mattress. An example of such pads is described in U.S. Pat. No. 10,357,197 to Smith, Jr. et al.

The under-mattress pressure-sensitive pad includes a sensing zone that is placed underneath the mattress. The sensing zone includes an electrically conductive material, like a wire, but has a resistance which decreases as pressure is applied. This allows for a resistance measuring circuit, such as a voltage divider, to be used with an Analog to Digital Converter (ADC) of a micro controller (MCU) to detect the presence of an object on the mattress. The variable resistance material may include one or more of a conductive film (e.g., a film called Velostat and produced by 3M, or any similar material), conductive foam, strain gauges which generate varying resistance when deformed, and conductive ink.

BRIEF SUMMARY OF EMBODIMENTS OF THE INVENTION

The inventors have found that with some variable resistance materials, such as inks, the manufacturing process is highly variable. Changes to aspects such as the thickness of the ink applied, the time to cure the ink, and the temperature during the curing process all have an effect on the final product. These variables lead to sensor materials which vary wildly in their final resistance response curves.

FIG. 1 shows an electrical diagram of a pad 100 known in the general art. The pad 100 has a sensing zone with variable resistor (hereinafter called "sensing resistor") with resistance $R_{SENSE}$ which decreases as pressure on the sensing zone increases.

The pad 100 further includes a signal generator 102, a resistor with a fixed resistance $R_{POT}$, and a microcontroller unit (MCU) 104 having an analog-to-digital converter (ADC) 106. The sensing zone is connected on one end to an electrical junction 108 and on the other end to a ground 100. The resistor with resistance $R_{POT}$ is connected on one end to the signal generator 102 and on the other end to the electrical junction 108. Finally, the electrical junction 108 is also connected to the ADC 106 of the MCU 104. Therefore, the circuit forms a voltage divider, with the voltage from the signal generator 102 applied to two resistors in series (the resistor with fixed resistance $R_{POT}$ and the variable sensing resistor with resistance $R_{SENSE}$), and the voltage being measured by the MCU at the junction 108 between the two resistors.

In this manner, once a signal is generated by the signal generator, the signal travels through the resistor with fixed resistance $R_{POT}$ to the junction 108. From the junction 108, the signal travels through the sensing zone ($R_{SENSE}$) to the ground 110, and also travels to the ADC 106.

The voltage of the portion of the signal that reaches the ADC and is measured by the ADC depends on $R_{SENSE}$. $R_{SENSE}$, in turn, depends on the pressure applied onto the sensing zone. Therefore, the voltage measured at the ADC is indicative of the pressure on the sensing zone, and can be processed to determine the presence and absence of an object on the sensing zone.

In a sample of ten ink-based pads pulled randomly from a population of 400 manufactured by the inventors, unloaded resistance values (resistance of the sensing zone with no weight on top) were found from 10 kOhms up to 98 kOhms. This variance is problematic as a voltage divider with a matching resistor ($R_{POT}$ in FIG. 1) is used for measuring the resistance of the pressure sensing material in the sensing zone. This matching resistor's value must be chosen to complement the resistance of the sensing material in the sensing zone to provide an optimal operating range for the system. Because of the substantial variance in the resistance of the sensing zone, mass production of under-mattress pressure-sensitive pad is problematic, as the resistance $R_{POT}$ of the matching resistor has to match the resistance values of the sensing zone. Since the resistance of the sensing zone varies substantially, the choice of the resistance $R_{POT}$ of the matching resistor may not allow optimal operating range for all sensing zones.

To illustrate this issue, FIG. 2 shows a sample response curve for two worst-case-scenario pads from the sample of the pads. The orange horizontal line 120 represents the maximum ADC voltage reading that the micro-controller can achieve. Curves 122 and 124 are response curves of a low-resistance pad (50 kOhm unloaded resistance) and of a high-resistance pad (120 kOhm unloaded resistance), respectively. As will be seen below, the voltage of the portion of the signal that reaches the ADC decreases as weight is placed on the sensing zone increases and $R_{SENSE}$ decreases. The further the response curve is from this line, the worse the sensitivity of the pad is. In this case the low resistance pad (curve 122) is approximately 50% less sensitive than the high resistance pad (curve 124).

The issue with using a voltage divider for a sensing circuit is the inherent effect of the signal being shifted away from the ADC max (or Vref) value. In the voltage divider equation, as shown in FIG. 1, it is desirable for Vout (the voltage measured at the ADC) to be as close to Vin (the voltage of the signal produced by the signal generator) as possible at calibration time to maintain maximum operating range for the readings at the ADC. Unfortunately, in the standard ADC setup Vref=Vin. This means the maximum Vout which can be obtained for any value of $R_{SENSE}$ is determined by $R_{POT}$.

$$Vout = Vin \frac{R_{SENSE}}{R_{POT} + R_{SENSE}}$$

As the value of $R_{SENSE}$ (the sensor material) decreases for a given $R_{POT}$, Vout begins to approach zero. This can be observed in FIG. 2, as the lower resistance pad's response curve 122 is shifted lower in the graph than the higher resistance pad's response curve 124.

Providing a lower $R_{POT}$ helps bring the response curve back up, but this can only be adjusted down so far. As $R_{POT}$ approaches zero ohms the battery drain of pad increases during normal operation, and selecting $R_{POT}$ to be zero negates the effects of a voltage divider entirely.

In order to resolve the above-mentioned issues that were found by the inventors of the present invention, in some embodiments of the present invention, the present invention, the matching resistor $R_{POT}$ in the voltage divider is a variable potentiometer which is controlled by the MCU. This allows for the matching resistance to be adjusted during the pad calibration to select a desired value that complements the actual resistor of the sensing zone. This helps mitigate the variances in the pad's sensor material by creating an adaptive circuit.

Additionally, in some embodiments of the present invention, Vref is set to be a desired voltage. This shifts the "ADC Max" line found in FIG. 1 downward toward the response curve of the pad. As will be shown further below, this shift enables the adaptive circuit to have a larger operating range to dynamically adjust the response curve of the pad.

Therefore, an aspect of some embodiments of the present invention relates to a pressure sensitive pad configured to be placed under a mattress and configured to identify presence and absence of a threshold weight on the mattress. The pressure sensitive pad includes a signal generator, a sensing zone, at least one variable matching resistor, a microcontroller unit (MCU). The signal generator is configured to generate an electrical signal. The sensing zone has a sensing resistor with a first resistance which varies depending on a pressure applied on sensing zone. The at least one variable matching resistor is in series with the sensing resistor and the signal generator and has a second resistance. The MCU has an analog-to-digital converter (ADC) configured for receiving and measuring a portion of the signal at an electrical junction between the sensing resistor an the at least one variable matching resistor. The MCU is configured to control the second resistance of the at least one variable matching resistor. The sensing zone is configured to be connected to an electrical ground. The pressure sensitive pad is configured to be calibrated to any mattress by: placing the sensing zone under the mattress with no additional weight in the mattress; generating an electrical signal via the signal generator; automatically measuring by the ADC a portion of the electrical signal reaching the ADC; automatically changing the second resistance of the at least one variable matching resistor via the microcontroller unit, until a desired value of the second resistance is found such that the portion of the signal reaching the ADC is within a predetermined range of a desired predetermined voltage. In operation, after calibration: the microcontroller unit is configured to set the second resistance to the desired value; the signal generator is configured to regularly generate electrical signals, which are configured to travel via the at least one variable matching resistor to the electrical junction, from the electrical junction to ADC, and from the electrical junction to the electrical ground via the sensing resistor, such that a portion of the signal reaching the ADC depends on the first resistance of the sensing resistor, such that the portion of the signal reaching the ADC can be processed to identify presence and absence of a threshold weight on the sensing zone.

In a variant, the at least one variable matching resistor comprises two variable matching resistors in series, each of the two variable matching resistors having a respective second resistance independently controlled by the microcontroller unit. The MCU is configured to automatically change the second resistance of the at least one variable matching resistor by: changing a first of the second resistances to reach a first desired value, whereby the portion of the signal reaching the ADC has a voltage within a predetermined coarse range of the desired voltage, while keeping a second of the first resistances fixed; maintaining the first of the second resistances fixed at the first desired value, and changing the second of the second resistances to reach a second desired value, whereby the portion of the signal reaching the ADC has a voltage within the predetermined range of the desired voltage, the predetermined range being smaller than the coarse predetermined range. In operation, the microcontroller unit is configured to set the first of the second resistances to the first desired value and to set the second of the second resistances to the second desired value.

In another variant, the pressure sensitive pad further comprises a third resistor in series with the at least one variable matching resistor, the third matching resistor having a fixed resistance.

In yet another variant, in operation, the MCU is further configured to determine whether calibration is valid, by: (i) starting a time period; (ii) at the end of the time period, performing a first check is to determine whether the measurements of the voltage at the ADC during a time period following calibration were consistently sufficiently above the predetermined desired voltage; (iii) if the check of step (ii) is positive, increasing the first desired value, and repeating all the steps from (i); (iv) of the check of step (iii) is negative, at the end of the time period, performing a second check is to determine whether the measurements of the voltage at the ADC during a time period following calibration were consistently sufficiently close to 0V; (v) if the check of step (iv) is positive, decreasing the first desired value, and repeating all the steps from (i); (vi) if the check of step (iv) is negative, determining that the calibration was correct.

The MCU may be further configured to repeat all steps from (i) after having performed step (vi).

Another aspect of some embodiments of the present invention relates to a method for calibrating a pressure sensitive pad configured to be placed under a mattress and configured to identify presence and absence of a threshold weight on the mattress. The method includes: (i) providing: a signal generator configured to generate an electrical signal; a sensing zone having a sensing resistor with a first resistance which varies depending on a pressure applied on sensing zone; at least one variable matching resistor in series with the sensing resistor and the signal generator, the variable matching resistor having a second resistance; a microcontroller unit (MCU) having an analog-to-digital converter (ADC) configured for receiving and measuring a portion of the signal at an electrical junction between the sensing resistor an the at least one variable matching resistor, the MCU being configured to control the second resistance of the at least one variable matching resistor; (ii) connecting the sensing zone to an electrical ground; (iii) placing the sensing zone under the mattress with no additional weight on the mattress; (iv) generating an electrical signal via the signal generator; (v) automatically measuring by the ADC a portion of the electrical signal reaching the ADC; (vi) automatically changing the second resistance of the at least one variable matching resistor via the microcontroller unit, until a desired value of the second resistance is found such that the portion of the signal reaching the ADC is within a predetermined range of a desired predetermined voltage.

In a variant, providing the at least one variable matching resistor comprises providing two variable matching resistors in series, each of the two variable matching resistors having a respective second resistances independently controlled by the microcontroller unit. Automatically changing the second resistance of the at least one variable matching resistor comprises: changing a first of the second resistances to reach a first desired value, whereby the portion of the signal reaching the ADC has a voltage within a predetermined coarse range of the desired voltage, while keeping a second of the first resistances fixed; maintaining the first of the second resistances fixed at the first desired value, and changing the second of the second resistances to reach a second desired value, whereby the portion of the signal reaching the ADC has a voltage within the predetermined range of the desired voltage, the predetermined range being smaller than the coarse predetermined range.

Yet another aspect of some embodiment of the present invention relates to a method of operating a pressure sensitive pad configured to be placed under a mattress and configured to identify presence and absence of a threshold weight on the mattress. The method includes: calibrating the pressure sensitive pad, as describe above; setting the second resistance to the desired value via the microcontroller unit; generating electrical signals, which are configured to travel via the at least one variable matching resistor to the electrical junction, from the electrical junction to ADC, and from the electrical junction to the electrical ground via the sensing resistor, such that a portion of the signal reaching the ADC depends on the first resistance of the sensing resistor; processing the portion of the signal reaching the ADC to identify presence and absence of a threshold weight on the sensing zone.

In a variant, providing the at least one variable matching resistor comprises providing two variable matching resistors in series, each of the two variable matching resistors having a respective second resistance independently controlled by the microcontroller unit. Automatically changing the second resistance of the at least one variable matching resistor comprises: changing a first of the second resistances to reach a first desired value, whereby the portion of the signal reaching the ADC has a voltage within a predetermined coarse range of the desired voltage, while keeping a second of the first resistances fixed; maintaining the first of the second resistances fixed at the first desired value, and changing the second of the second resistances to reach a second desired value, whereby the portion of the signal reaching the ADC has a voltage within the predetermined range of the desired voltage, the predetermined range being smaller than the coarse predetermined range; setting the second resistance to the desired value via the microcontroller unit comprises setting the first of the second resistances to the first desired value and setting the second of the second resistances to the second desired value.

In another variant, the method further comprises determining whether calibration is valid, by: (a) starting a time period; (b) at the end of the time period, performing a first check is to determine whether the measurements of the voltage at the ADC during a time period following calibration were consistently sufficiently above the predetermined desired voltage; (c) if the check of step (b) is positive, increasing the first value, and repeating all the steps from (a); (d) of the check of step (c) is negative, at the end of the time period, performing a second check is to determine whether the measurements of the voltage at the ADC during a time period following calibration were consistently sufficiently close to 0V; (e) if the check of step (d) is positive, decreasing the desired value, and repeating all the steps from (a); (f) if the check of step (d) is negative, determining that the calibration was correct.

In a variant, the method further comprising, after step (f): repeating all steps from step (a).

BRIEF DESCRIPTION OF DRAWINGS

FIG. 1 is a circuit drawing of an under-mattress pressure-sensitive pad as known in the general art;

FIG. 2 is a graph of response curves of under-mattress pressure-sensitive pads of the general art having different unloaded resistance values, as discovered by the inventors;

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 3:
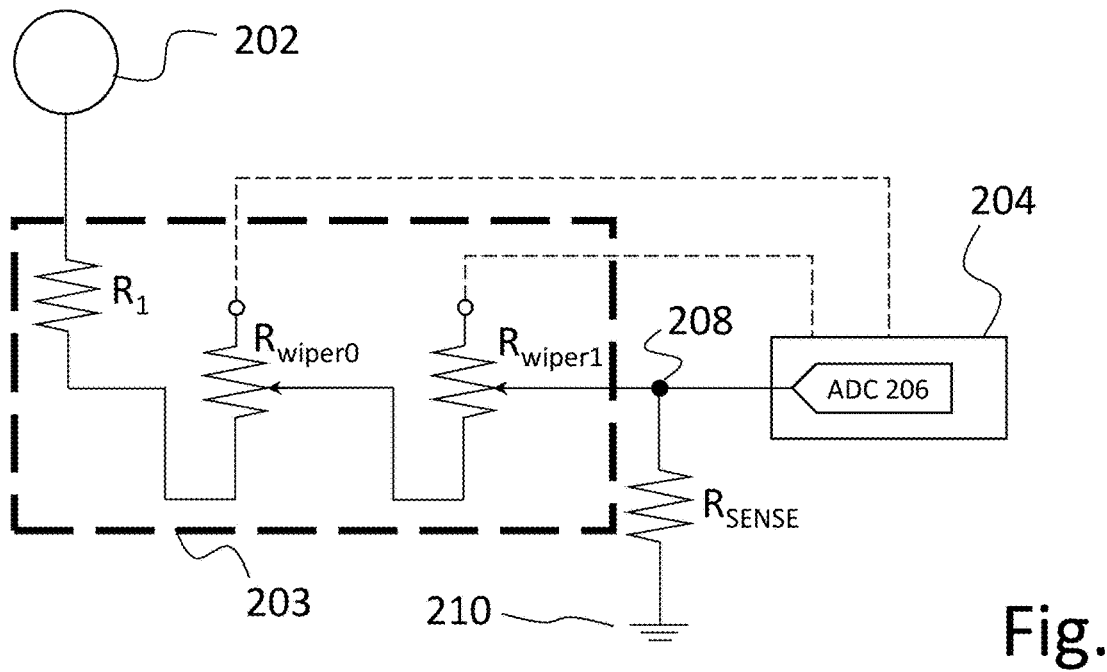
FIG. 3 is a circuit drawing of an under-mattress pressure-sensitive pad, with an adaptive voltage divider having at least one variable resistor controlled by the MCU, according to some embodiments of the present invention.

FIG. 3 is a circuit drawing of an under-mattress pressure-sensitive pad 200, forming an adaptive voltage divider having at least one variable resistor controlled by the MCU, according to some embodiments of the present invention.

The pressure sensitive pad 200 includes a signal generator 202, a sensing zone, at least one variable matching resistor, a microcontroller unit (MCU) 204 having an analog-to-digital converter (ADC) 206.

The signal generator 202 is configured to generate an electrical signal having a predetermined voltage (Vin). The sensing zone has a sensing resistor with a first resistance $R_{SENSE}$ which varies depending on a pressure applied on the sensing zone. More specifically, the resistance $R_{SENSE}$ decreases as the pressure on the sensing zone increases.

The variable matching resistor(s) is (are) in series with the sensing resistor and the signal generator 202. Each variable matching resistor is controlled by the MCU 204. In the embodiment in which one variable resistor is present, the variable matching resistor having a second resistance Rwiper0. In some embodiments of the present invention, a plurality of variable matching resistors are present. In a non-limiting example, two variable matching resistors having a second resistance Rwiper0 and Rwiper1, respectively, are present. In some embodiments of the present invention, a fixed resistor with resistance R1 is also present. In other words, a matching resistor apparatus 203 is located in series with the sensing resistor with first resistance $R_{SENSE}$. The matching resistor apparatus 203 includes one or more variable matching resistors each controlled by the MCU, and optionally one or more fixed resistors.

In a non-limiting example, for a signal generated by the signal generator and having voltage of about 3.3V, the two variable matching resistors were chosen to be 100 k ohm potentiometer chips, to enable a 0-200 k ohm adjustment range in 512 steps. The fixed resistor with resistance R1 was chosen to be small (1 k ohm) to allow the potentiometer to have the largest effect on the circuit. It should be noted that the number, type, and resistance values of the variable matching resistors and of the fixed resistor in the matching resistor apparatus 203 and the voltage of the signal generated by signal generator 202 can be changed according to different requirements of the pad without departing from the spirit of the invention.

The potentiometer chips were interfaced to the MCU via an SPI data bus. This allows the micro-controller to adjust both potentiometers to any available increment with a single data command, thereby speeding up the discovery of a correct value. This could also be accomplished using an up/down potentiometer chip, but would result in increased logic required to put the potentiometer into a known-good state and to longer search time to locate the correct value.

The microcontroller unit (MCU) 204 has an analog-to-digital converter (ADC) 206 configured for receiving and measuring a portion of the signal at the electrical junction 208 between the sensing resistor and matching resistor apparatus 203. The MCU 204 is configured to control the second resistance of the at least one variable matching resistor.

Figure 7:
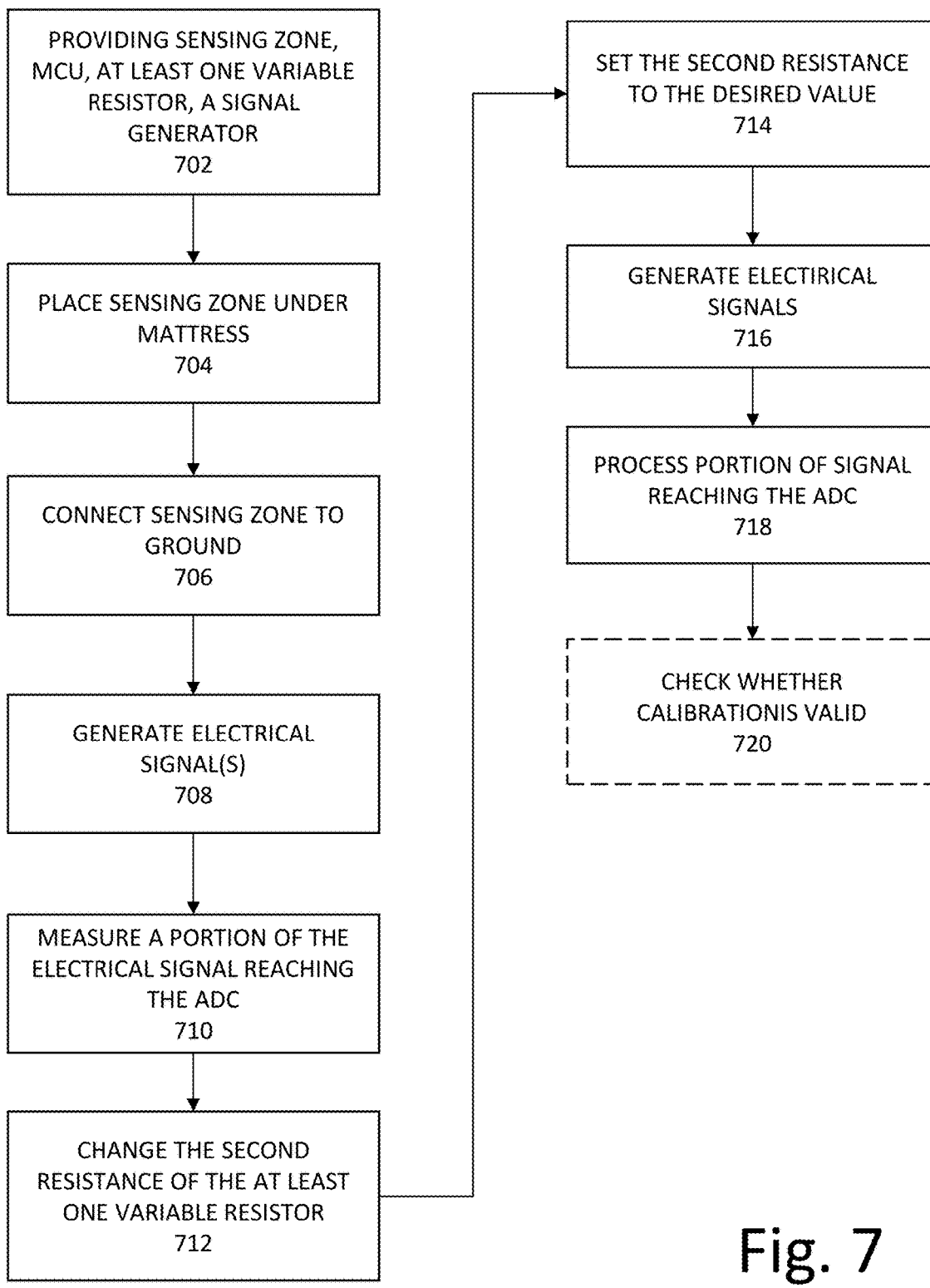
FIG. 7 is a flowchart of a method for calibrating and using an under-mattress pressure-sensitive pad, with an adaptive voltage divider, according to some embodiments of the present invention.

Referring now to FIG. 7, a flowchart 700 of a method for calibrating and using an under-mattress pressure-sensitive pad with an adaptive voltage divider of FIG. 1, according to some embodiments of the present invention.

At 702, the signal generator, sensing zone, MCU with ADC, and a matching resistor apparatus are provided, as explained above.

At 704, the sensing zone is placed under a mattress.

At 706, the sensing zone is electrically connected to an electrical ground.

At 708, an electrical signal with a predetermined voltage is generated via the signal generator.

At 710, the ADC automatically measures a portion of the electrical signal reaching the ADC.

At 712, the overall resistance of the matching resistor apparatus is automatically changed by the MCU, until a desired value of the matching resistor apparatus is found, such that the portion of the signal reaching the ADC is within a predetermined range of a desired predetermined voltage.

In some embodiments of the present invention, the matching resistance apparatus includes one variable resistor. In these embodiments, the resistance of the variable matching resistor is changed in order to bring the voltage of the signal at the ADC within a desired range to a predetermined desired voltage.

In some embodiments of the present invention, the matching resistance apparatus includes two variable resistors in series. One having a resistance Rwiper0 and the one having a resistance Rwiper1 (as shown in FIG. 3). In such embodiments, both Rwiper0 and Rwiper1 are changed independently from each other by the MCU in order to bring the voltage of the signal at the ADC within a desired range to a predetermined desired voltage. In some embodiments of the present invention, the Rwiper0 is changed, while maintaining Rwiper1 fixed at an initial resistance, until a value of Rwiper0 is found where the voltage of the signal at the ADC is within a coarse range of the predetermined desired voltage. Then, Rwiper0 is maintained at the value that was previously found, and Rwiper1 is tweaked to bring the voltage at the ADC even closer to the predetermined desired voltage, within a fine range of the predetermined desired voltage. The fine range is smaller than the coarse range. This enables better control of the matching voltage and a final value of Vout (the voltage measured at the ADC) that is closer to the desired value.

At 714, after calibration is completed, the microcontroller unit is configured to set the second resistance of the matching resistor apparatus 203 (of FIG. 3) at the value found during calibration.

At 716, the signal generator is configured to regularly generate electrical signals, which are configured to travel via the matching resistor apparatus to the electrical junction, from the electrical junction to ADC, and from the electrical junction to the electrical ground via the sensing resistor, such that a portion of the signal reaching the ADC depends on the first resistance of the sensing resistor.

At 718, the portion of the signal reaching the ADC is processed to identify presence and absence of a threshold weight on the sensing zone.

In some embodiments of the present invention, at 720, the microcontroller unit is configured to check whether the calibration was performed correctly or is valid after a period of time in which the sensitive zone pad may have degraded. This check may be performed during an initial period of the operation of the pad, periodically, or continuously. If some conditions are met, which indicate that the calibration was performed incorrectly (as will be discussed further below, with reference to FIG. 8) the MCU is configured to change the second resistance of the matching resistor apparatus 203 (of FIG. 3) over time, during the use of the pad, in order to correct the calibration.

Figure 4:
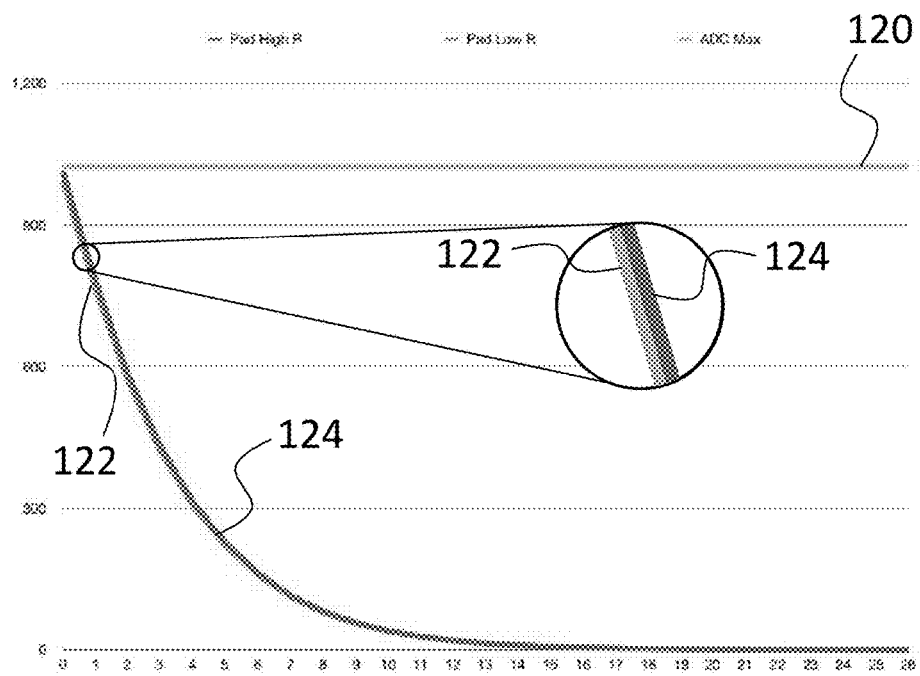
FIG. 4 is a graph of response curves of under-mattress pressure-sensitive pads having different unloaded resistance values and adaptive voltage dividers, according to some embodiments of the present invention.

FIG. 4 is a graph of response curves of under-mattress pressure-sensitive pads having different unloaded resistance values and adaptive voltage dividers, according to some embodiments of the present invention.

The matching resistor(s) in the voltage divider allows for the matching resistance to be adjusted during the pad calibration stage to select a desired ideal value. This helps mitigate the variances in the sensor material of the sensing zone by creating an adaptive circuit. This was applied to the same two pads used in FIG. 2 and results in the response curves found in FIG. 4.

It can be easily seen that the response curves 122 and 124 in FIG. 4 are almost identical to each other. The curves 122 and 124 are also both lifted much closer to the ADC max reading line 120. This vertical shift is partly due to the dynamic resistance calibration described above.

The vertical shift is also aided by lowering the reference voltage (ADC Max voltage) of the MCU to a desired level. For example, if the voltage of the signal generated by the signal generator is 3.3 V, the reference voltage chosen can be lowered to about 1 V. Thus. The ADC max line is shifted downward.

This by itself does not fix the issue, but it does allow the dynamic resistance calibration of the adaptive voltage divider to have a larger operating range to dynamically adjust the response curve.

As an example, reference is made to the values in Table 1, in which the voltage at the ADC is measured for different combinations of unloaded $R_{SENSE}$ and Rwiper0 (in the embodiments in which a single matching resistor is present). If the goal were to achieve Vref of 3.3 volt, which is the maximal voltage at the ADC when $R_{SENSE}$ is much higher than the matching resistance, these Vref values are all clustered in the upper left portion of the table. Thus, if $R_{SENSE}$ is above 30 kOhm, Rwiper0 can only change between 1 kOhm and 2 kOhm for the response curves to be raised to Vref and increase the sensitivity of the pad. Higher values of Rwiper0 will not be able to complement lower values of unloaded $R_{SENSE}$ to shift the response curve to reach about 3.3 V.

If, instead, the target Vref is around 1 volt, it can be seen from the table that the 1 V values cut through the center of our table, giving a better chance of reaching the target voltage. Therefore, even if $R_{SENSE}$ falls below 30 kOhm (even down to 500 Ohm), Rwiper0 can be raised up to 100 kOhm to raise the response curve to approach Vref, and therefore maintain higher sensitivity.

in the lower half of the array. If the target value is greater than the element, the search continues in the upper half of the array. By doing this, the binary search technique eliminates the half in which the target value cannot lie in each iteration.

The above description of a binary search is applicable to the search for the desired voltage at the ADC of the present invention, except instead of a sorted array potentiometer steps are used and the "target value" is the voltage returned by the ADC.

At the beginning of the calibration cycle, all variable matching resistors are set to their midpoints to establish a known good condition and in preparation for the next step. The MCU then begins to perform a binary search to establish a target ADC value of about 1 V, or within a certain range (e.g., ±0.1 V) of 1 V.

This process is performed on the first variable matching resistor, to determine its desired resistance. Once this is complete, if present in the circuit, additional variable matching resistors are each iterated through to find their desired values.

Figure 5:
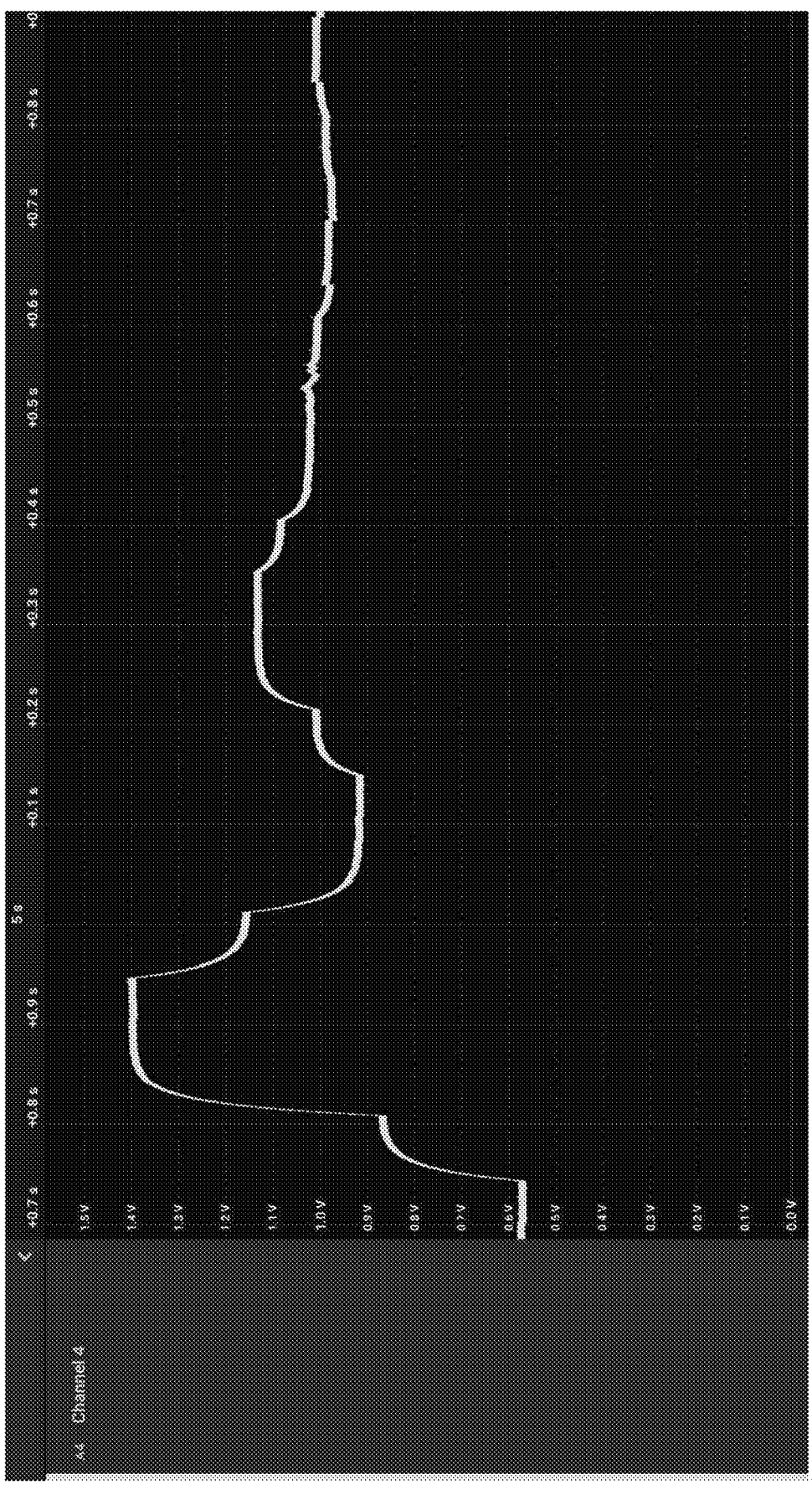
FIG. 5 is a graph showing a binary search for a predetermined desired voltage at the ADC with a single variable resistor, according to some embodiments of the present invention.

An example of a simpler single potentiometer implementation can be seen in FIG. 5. At the beginning of the calibration cycle (designated by Marker A1) the potentiometer is set to its midpoint value (100 kOhm). A binary search is then performed, changing Rwiper0 to narrow down the voltage measured at the ADC to the desired value of (0.9±0.1) V (i.e., within 0.1 V of the desired value of 1 V) in eight steps. In this case, the binary search was completed in about 12 ms.

Figure 6:
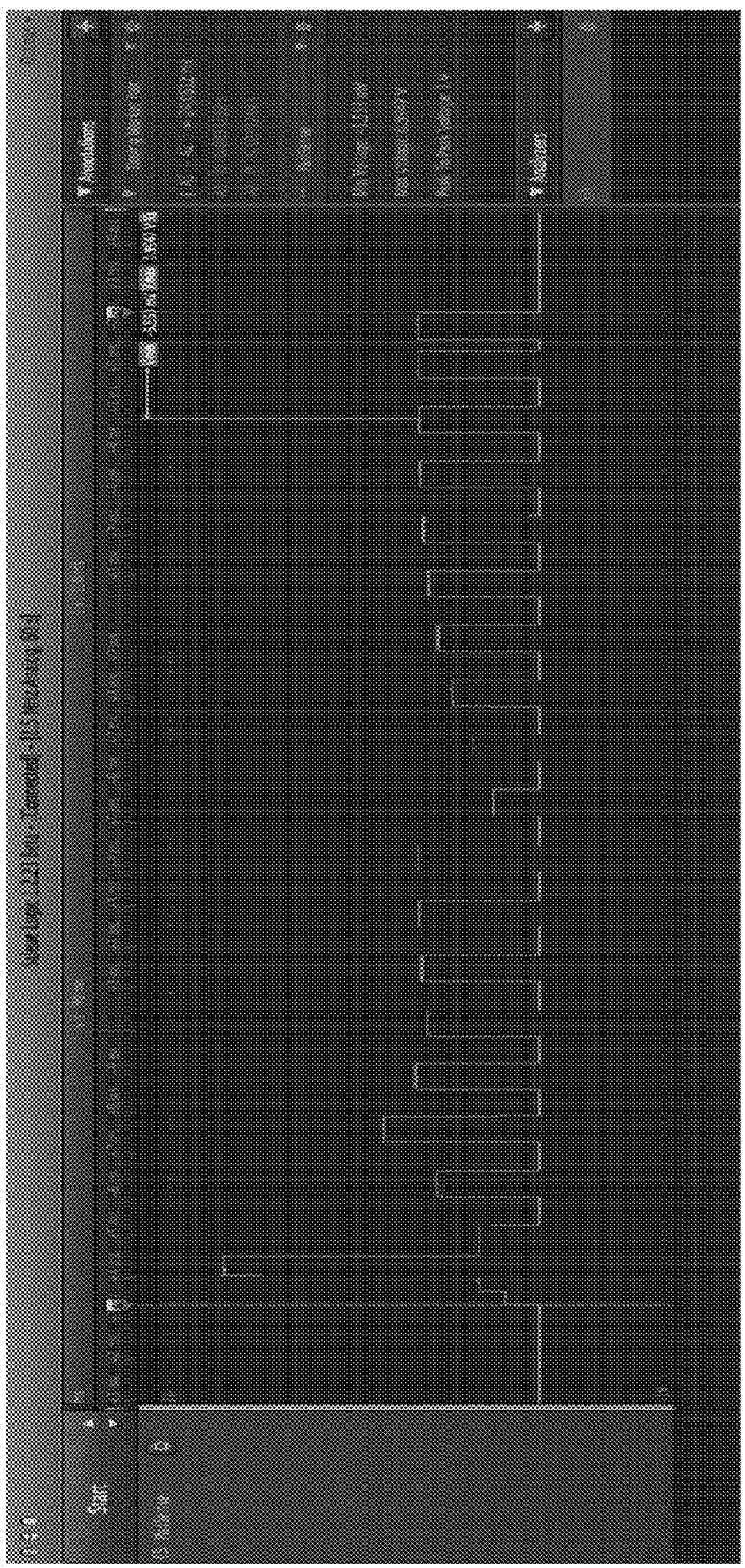
FIG. 6 is a graph showing a binary search for a predetermined desired voltage at the ADC with two variable resistors, according to some embodiments of the present invention.

For comparison, FIG. 6 shows signals from the MCU to the potentiometers during a potentiometer calibration implemented with dual variable matching resistors. Each signal pulse is the result of an instruction to the respective potentiometer to either increase or decrease resistance, according to the binary search technique described above. A single

TABLE 1

| Rwiper0 $R_{SENSE}$ | 1,000 | 2,000 | 4,000 | 6,000 | 8,000 | 10,000 | 20,000 | 30,000 | 40,000 | 50,000 | 60,000 | 70,000 | 80,000 | 90,000 | 100,000 |
|---|---|---|---|---|---|---|---|---|---|---|---|---|---|---|---|
| 50,000 | 3.24 | 3.17 | 3.06 | 2.95 | 2.84 | 2.75 | 2.36 | 2.00 | 1.83 | 1.65 | 1.50 | 1.38 | 1.27 | 1.18 | 1.10 |
| 40,000 | 3.22 | 3.14 | 3.00 | 2.87 | 2.75 | 2.64 | 2.20 | 1.89 | 1.65 | 1.47 | 1.32 | 1.20 | 1.10 | 1.02 | 0.94 |
| 30,000 | 3.19 | 3.09 | 2.91 | 2.75 | 2.61 | 2.48 | 1.98 | 1.65 | 1.41 | 1.24 | 1.10 | 0.99 | 0.90 | 0.83 | 0.76 |
| 20,000 | 3.14 | 3.00 | 2.75 | 2.54 | 2.36 | 2.20 | 1.63 | 1.32 | 1.10 | 0.94 | 0.83 | 0.73 | 0.66 | 0.60 | 0.55 |
| 10,000 | 3.00 | 2.75 | 2.36 | 2.06 | 1.83 | 1.66 | 1.10 | 0.83 | 0.66 | 0.56 | 0.47 | 0.41 | 0.37 | 0.33 | 0.30 |
| 8,000 | 2.93 | 2.64 | 2.20 | 1.80 | 1.65 | 1.47 | 0.94 | 0.69 | 0.55 | 0.46 | 0.39 | 0.34 | 0.30 | 0.27 | 0.24 |
| 4,000 | 2.64 | 2.20 | 1.65 | 1.32 | 1.10 | 0.94 | 0.55 | 0.39 | 0.30 | 0.24 | 0.21 | 0.18 | 0.16 | 0.14 | 0.13 |
| 2,000 | 2.20 | 1.65 | 1.10 | 0.83 | 0.66 | 0.55 | 0.30 | 0.21 | 0.16 | 0.13 | 0.11 | 0.09 | 0.08 | 0.07 | 0.06 |
| 1,000 | 1.65 | 1.10 | 0.66 | 0.47 | 0.37 | 0.30 | 0.16 | 0.11 | 0.08 | 0.06 | 0.05 | 0.05 | 0.04 | 0.04 | 0.03 |
| 500 | 1.10 | 0.66 | 0.37 | 0.25 | 0.10 | 0.10 | 0.08 | 0.05 | 0.04 | 0.03 | 0.03 | 0.02 | 0.02 | 0.02 | 0.02 |

FIGS. 5 and 6 refer to binary searches for the predetermined desired voltage at the ADC. FIG. 5 is a graph showing a binary search for a predetermined desired voltage at the ADC with a single variable resistor, according to some embodiments of the present invention. FIG. 6 is a graph showing a binary search for a predetermined desired voltage at the ADC with two variable resistors, according to some embodiments of the present invention.

In some embodiments, the one or more variable matching resistors are changed via the binary search technique to find the predetermined desired voltage at the ADC in the calibration.

Binary search begins by comparing an element in the middle of the array with the target value. If the target value matches the element, its position in the array is returned. If the target value is less than the element, the search continues signal starts when a sharp increase from 0V as the sensor circuit is energized, reaches a positive value, and flattens at the positive value at which point the calibration logic takes its reading for the binary search. The sensor circuit is then de-energized and the signal sharply decreases from the positive value to 0V while the potentiometers are adjusted for the next step of the calibration process.

Once again, the midpoints of both matching resistors are set and, using the timescale at the top of the figure, the Rwiper0 binary search begins at time 6.085 seconds and ends at time 6.094 seconds (for a total of 9 ms). Then, maintaining Rwiper0 at the value found in the first binary search, the binary search for Rwiper1 then begins at time 6.095 seconds and completes by time 6.105 seconds (for a total of another 10 ms).

At the end of this double potentiometer calibration value search, the voltage at the ADC voltage is 0.9947 volts, which is just below the target of 1 volt, within a period of 20 ms. Compared to the single potentiometer search, it can be seen that implementing this system as a dual potentiometer configuration results in a more accurate final voltage at the cost of a longer calibration time. Since this time is still small enough to not be observable to the end user, the tradeoff is very good. In addition the inclusion of a second potentiometer allows the circuit to adjust to a much wider range of pressure response curves, allowing the circuit to accommodate a larger tolerance of variations created during the manufacturing process of the pad.

In preliminary tests performed by the inventors, graduated weights were placed directly on the pressure sensitive ink. When these tests were performed without the variable matching resistors of the present invention and without setting the voltage of the ADC at the desired target, the minimum weight that had to be added before seeing a measurable difference in the reaction of the pad was 100 grams.

Performing this exact test again using the new dual potentiometer circuit with 1 volt targets, the inventors found that the minimum weight to be added before seeing a measurable difference in the reaction of the pad was now 1 gram.

This test measured the weight response of the pad's material and the pad's circuit. This test proved that the circuit of the present invention had much better fidelity than previously used pad circuitry.

Figure 8:
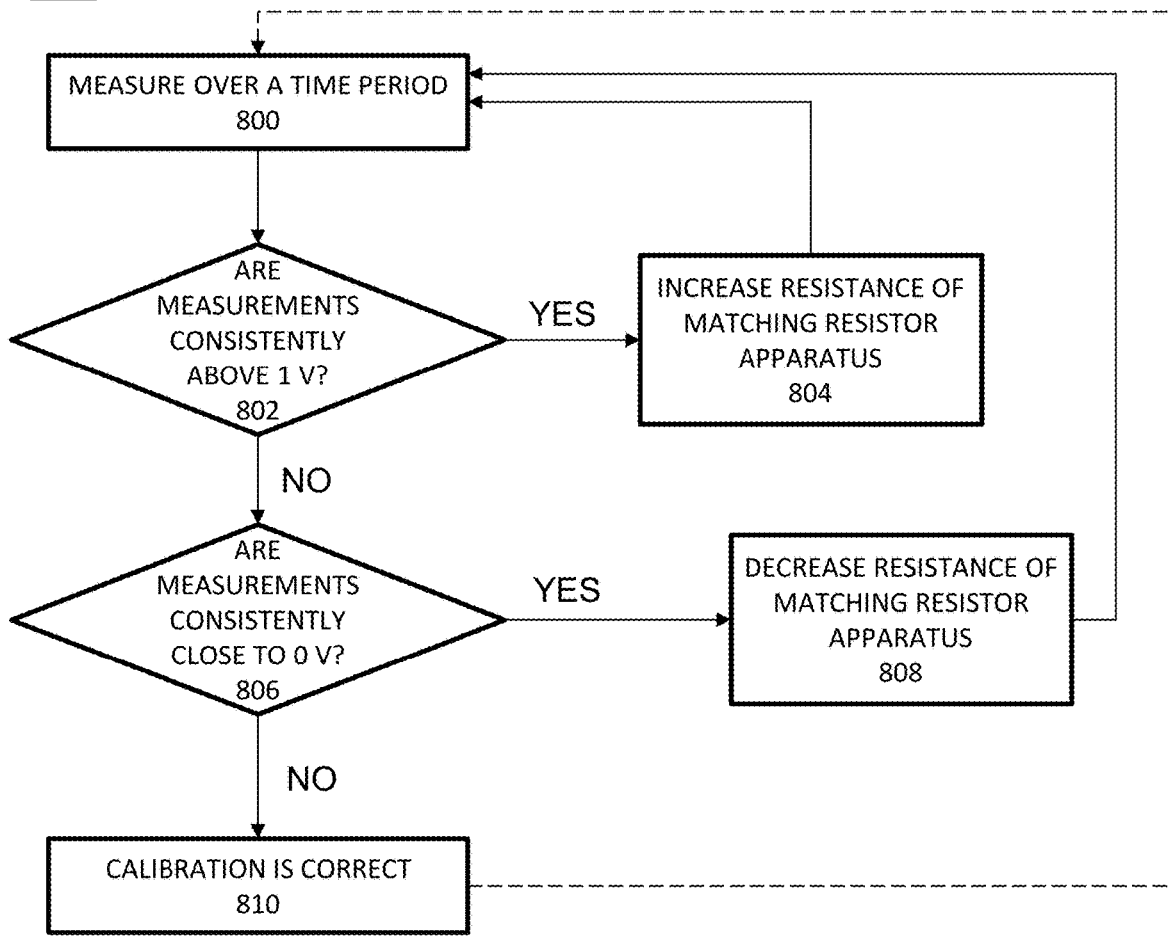
FIG. 8 is a flowchart of a method for adjusting an incorrect calibration of an under-mattress pressure-sensitive pad, according to some embodiments of the present invention.

FIG. 8 is a flowchart of a method for adjusting an incorrect calibration of an under-mattress pressure-sensitive pad, according to some embodiments of the present invention.

Pads are meant to be calibrated before use only with the mattress above the sensing zone. However, field tests by the inventors concluded that pads were sometimes not correctly calibrated before use or users sometimes forgot to calibrate the pad before use.

As an example, if a staff member calibrated the pad with a patient on the mattress before use, then during use the pad would detect an extra heavy mattress and would miss the patient's exit from the bed. On the reverse, if a staff member calibrated the pad without a mattress prior to use, then during use the weight of the mattress would be detected by the pad as the weight of a person to the pad, and may cause the pad to detect the patient's exit from the bed, even when the patient is on the bed.

With the new potentiometer-based calibration system, a new check can be made after calibration, to determine whether the initial calibration was correct.

With the pad of the present invention, a mattress without a patient should cause the pad to generate a signal of a predetermined voltage (e.g., 1 volt) at the ADC, while a mattress with a patient should cause the pad to generate a signal near 0 volts (but not at 0 volts) at the ADC.

This means that if a reading above 1 volt is consistently measured at the ADC over a period of time, then too much weight has been removed from the pad. This is possibly an indication of a pad that was miscalibrated, by having a person on the mattress during calibration.

On the other hand, if a reading around 0 volts is consistently measured at the ADC over a period of time, then too much weight has been applied on the pad. This is possibly an indication of a pad that was miscalibrated, by not placing the mattress on the sensing zone during calibration.

After detecting the above-mentioned potential miscalibrations, adjusting the variable matching resistors too much or too quickly is undesirable, as both of the above scenarios (voltage about 1V or at 0V) may legitimately occur for a brief period. For example, the voltage at the ADC may be above 1V for a brief time period, if the mattress is lifted when the sheets are changed. Or, the voltage at the ADC may be 0, if a weight, such as another person sitting on the bed in addition to the patient, is placed on the mattress.

To address this, in some embodiments of the present invention, after calibration is complete, if the above-mentioned scenarios occur, the voltage of the variable matching resistor apparatus is changed by one step every few minutes, to change the voltage of the ADC and bring the voltage at the ADC within a desired range. During testing by the inventors, this resulted in a miscalibrated pad typically fixing itself within 30 minutes after pressure was either applied to or removed from the pad (based on the type of miscalibration that occurred).

Therefore, at 800, after calibration, the voltage at the ADC is measured over several times over a period of time. The period of time may be a few minutes, for example, such as 2, 3, 5, or 6 minutes, for example. It should be noted that any length of the time period is within the scope of the present invention.

At 802, a check is made to determine whether the measurements of the voltage at the ADC during the time period were consistently sufficiently above the predetermined desired voltage (for example, more than 0.1 V above 1 V). "Consistently" may be defined as any chosen fraction of the measurements, chosen a priori, such as 40% or above, 50% or above, etc. If this is the case, the resistance of the matching resistance apparatus is increased at 804, and a new time period is started.

If the measurements of the voltage at the ADC in the time period were not consistently sufficiently above the predetermined desired voltage at 802, a new check is made at 806 to determine if measurements of the voltage at the ADC were consistently close to 0 V (e.g., below 0.1 V) during the time period. "Consistently" may be defined as any chosen fraction of the measurements, chosen a priori, such as 40% or above, 50% or above, etc. If this is the case, the resistance of the matching resistance apparatus is decreased at 808, and a new time period is started.

If at 806, the measurements of the voltage at the ADC in the time period were not consistently sufficiently near 0 V, it is determined that the calibration is correct at 810.

It should be noted that the use of the sub-method 720 may not be restricted to the period after the calibration alone or when user activity is detected. In fact, over time, the variable resistive material of the pad's sensing zone may degrade and become less sensitive to pressure, thereby generating measurements indicative of the person's absence from the mattress even when the person is on the mattress. Therefore, the sub-method 720 may be used periodically or continuously to assess the validity of the initial calibration and to correct for the degradation of the material of the pad's sensing zone. The dotted arrow leading from step 810 back to step 800 shows the embodiment in which the sub-method 720 is performed periodically or continuously, even after the calibration was deemed to be correct in a previous cycle.

Although the invention is described above in terms of various exemplary embodiments and implementations, it should be understood that the various features, aspects, time measurements, and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

The invention claimed is:

1. A pressure sensitive pad configured to be placed under a mattress and configured to identify presence and absence of a threshold weight on the mattress, the pressure sensitive pad comprising:
a signal generator configured to generate an electrical signal;
a sensing zone having a sensing resistor with a first resistance which varies depending on a pressure applied on sensing zone;
at least one variable matching resistor in series with the sensing resistor and the signal generator, the variable matching resistor having a second resistance;
a microcontroller unit (MCU) having an analog-to-digital converter (ADC) configured for receiving and measuring a portion of the signal at an electrical junction between the sensing resistor an the at least one variable matching resistor, the MCU being configured to control the second resistance of the at least one variable matching resistor;
wherein:
the sensing zone is configured to be connected to an electrical ground;
the pressure sensitive pad is configured to be calibrated to any mattress by:
placing the sensing zone under the mattress with no additional weight in the mattress;
generating an electrical signal via the signal generator;
automatically measuring by the ADC a portion of the electrical signal reaching the ADC;
automatically changing the second resistance of the at least one variable matching resistor via the microcontroller unit, until a desired value of the second resistance is found such that the portion of the signal reaching the ADC is within a predetermined range of a desired predetermined voltage;
wherein, in operation, after calibration:
the microcontroller unit is configured to set the second resistance to the desired value;
the signal generator is configured to regularly generate electrical signals, which are configured to travel via the at least one variable matching resistor to the electrical junction, from the electrical junction to ADC, and from the electrical junction to the electrical ground via the sensing resistor, such that a portion of the signal reaching the ADC depends on the first resistance of the sensing resistor, such that the portion of the signal reaching the ADC can be processed to identify presence and absence of a threshold weight on the sensing zone.

2. The pressure sensitive pad of claim 1, wherein:
the at least one variable matching resistor comprises two variable matching resistors in series, each of the two variable matching resistors having a respective second resistance independently controlled by the microcontroller unit;
the MCU is configured to automatically change the second resistance of the at least one variable matching resistor by:
changing a first of the second resistances to reach a first desired value, whereby the portion of the signal reaching the ADC has a voltage within a predetermined coarse range of the desired voltage, while keeping a second of the first resistances fixed;
maintaining the first of the second resistances fixed at the first desired value, and changing the second of the second resistances to reach a second desired value, whereby the portion of the signal reaching the ADC has a voltage within the predetermined range of the desired voltage, the predetermined range being smaller than the coarse predetermined range;
and
in operation, the microcontroller unit is configured to set the first of the second resistances to the first desired value and to set the second of the second resistances to the second desired value.

3. The pressure sensitive pad of claim 1, further comprising a third resistor in series with the at least one variable resistor, the third matching resistor having a fixed resistance.

4. The pressure sensitive pad of claim 1, wherein, in operation, the MCU is further configured to determine whether calibration is valid, by:
(i) starting a time period;
(ii) at the end of the time period, performing a first check is to determine whether the measurements of the voltage at the ADC during a time period following calibration were consistently sufficiently above the predetermined desired voltage;
(iii) if the check of step (ii) is positive, increasing the first desired value, and repeating all the steps from (i);
(iv) of the check of step (iii) is negative, at the end of the time period, performing a second check is to determine whether the measurements of the voltage at the ADC during a time period following calibration were consistently sufficiently close to 0V;
(v) if the check of step (iv) is positive, decreasing the first desired value, and repeating all the steps from (i);
(vi) if the check of step (iv) is negative, determining that the calibration was correct.

5. The pressure sensitive pad of claim 4, wherein the MCU is configured to repeat all steps from (i) after having performed step (vi).

6. A method for calibrating a pressure sensitive pad configured to be placed under a mattress and configured to identify presence and absence of a threshold weight on the mattress, method comprising:
(i) providing:
a signal generator configured to generate an electrical signal;
a sensing zone having a sensing resistor with a first resistance which varies depending on a pressure applied on sensing zone;
at least one variable matching resistor in series with the sensing resistor and the signal generator, the variable matching resistor having a second resistance;
a microcontroller unit (MCU) having an analog-to-digital converter (ADC) configured for receiving and measuring a portion of the signal at an electrical junction between the sensing resistor an the at least one variable matching resistor, the MCU being configured to control the second resistance of the at least one variable matching resistor;
(ii) connecting the sensing zone to an electrical ground;
(iii) placing the sensing zone under the mattress with no additional weight on the mattress;
(iv) generating an electrical signal via the signal generator;

(v) automatically measuring by the ADC a portion of the electrical signal reaching the ADC;
(vi) automatically changing the second resistance of the at least one variable matching resistor via the microcontroller unit, until a desired value of the second resistance is found such that the portion of the signal reaching the ADC is within a predetermined range of a desired predetermined voltage.

7. The method of claim 6, wherein:
providing the at least one variable matching resistor comprises providing two variable matching resistors in series, each of the two variable matching resistors having a respective second resistances independently controlled by the microcontroller unit;
automatically changing the second resistance of the at least one variable matching resistor comprises:
  changing a first of the second resistances to reach a first desired value, whereby the portion of the signal reaching the ADC has a voltage within a predetermined coarse range of the desired voltage, while keeping a second of the first resistances fixed;
  maintaining the first of the second resistances fixed at the first desired value, and changing the second of the second resistances to reach a second desired value, whereby the portion of the signal reaching the ADC has a voltage within the predetermined range of the desired voltage, the predetermined range being smaller than the coarse predetermined range.

8. A method of operating calibrating a pressure sensitive pad configured to be placed under a mattress and configured to identify presence and absence of a threshold weight on the mattress, method comprising:
calibrating the pressure sensitive pad according to the method of claim 6;
setting the second resistance to the desired value via the microcontroller unit;
generating electrical signals, which are configured to travel via the at least one variable matching resistor to the electrical junction, from the electrical junction to ADC, and from the electrical junction to the electrical ground via the sensing resistor, such that a portion of the signal reaching the ADC depends on the first resistance of the sensing resistor;
processing the portion of the signal reaching the ADC to identify presence and absence of a threshold weight on the sensing zone.

9. The method of claim 8, wherein:
providing the at least one variable matching resistor comprises providing two variable matching resistors in series, each of the two variable matching resistors having a respective second resistance independently controlled by the microcontroller unit;
automatically changing the second resistance of the at least one variable matching resistor comprises:
  changing a first of the second resistances to reach a first desired value, whereby the portion of the signal reaching the ADC has a voltage within a predetermined coarse range of the desired voltage, while keeping a second of the first resistances fixed;
  maintaining the first of the second resistances fixed at the first desired value, and changing the second of the second resistances to reach a second desired value, whereby the portion of the signal reaching the ADC has a voltage within the predetermined range of the desired voltage, the predetermined range being smaller than the coarse predetermined range;
and
setting the second resistance to the desired value via the microcontroller unit comprises setting the first of the second resistances to the first desired value and setting the second of the second resistances to the second desired value.

10. The method of claim 8, further comprising determining whether calibration is valid, by:
(a starting a time period;
b) at the end of the time period, performing a first check is to determine whether the measurements of the voltage at the ADC during a time period following calibration were consistently sufficiently above the predetermined desired voltage;
(c) if the check of step (b) is positive, increasing the first value, and repeating all the steps from (a);
(d) of the check of step (c) is negative, at the end of the time period, performing a second check is to determine whether the measurements of the voltage at the ADC during a time period following calibration were consistently sufficiently close to 0V;
(e) if the check of step (d) is positive, decreasing the desired value, and repeating all the steps from (a);
(f) if the check of step (d) is negative, determining that the calibration was correct.

11. The method of claim 10, further comprising, after step (f): repeating all steps from step (a).

* * * * *